United States Patent
Fell

(10) Patent No.: US 8,956,367 B2
(45) Date of Patent: Feb. 17, 2015

(54) SYSTEM AND METHOD FOR SHAPING AN ANATOMICAL COMPONENT

(76) Inventor: Barry M. Fell, Hummelstown, PA (US)

( * ) Notice: Subject to any disclaimer, the term of this patent is extended or adjusted under 35 U.S.C. 154(b) by 1361 days.

(21) Appl. No.: 12/090,290

(22) PCT Filed: Nov. 9, 2006

(86) PCT No.: PCT/US2006/043606
§ 371 (c)(1),
(2), (4) Date: Apr. 15, 2008

(87) PCT Pub. No.: WO2007/056506
PCT Pub. Date: May 18, 2007

(65) Prior Publication Data
US 2008/0281335 A1    Nov. 13, 2008

Related U.S. Application Data

(60) Provisional application No. 60/734,857, filed on Nov. 9, 2005.

(51) Int. Cl.
A61B 17/56    (2006.01)
A61B 19/00    (2006.01)
A61B 17/00    (2006.01)
A61B 17/16    (2006.01)
A61B 17/88    (2006.01)
A61B 17/32    (2006.01)
A61B 17/34    (2006.01)

(52) U.S. Cl.
CPC ....... *A61B 19/5244* (2013.01); *A61B 17/00491* (2013.01); *A61B 17/1675* (2013.01); *A61B 17/8805* (2013.01); *A61B 19/22* (2013.01); *A61B 19/52* (2013.01); *A61B 17/32* (2013.01); *A61B 17/32002* (2013.01); *A61B 19/2203* (2013.01); *A61B 19/50* (2013.01); *A61B 2017/005* (2013.01); *A61B 2017/3447* (2013.01)
USPC .......................................................... 606/94

(58) Field of Classification Search
USPC ................. 700/186, 163, 159, 245; 606/128; 318/568.11; 144/3.1; 83/76.8, 367, 83/370; 451/5
See application file for complete search history.

(56) References Cited

U.S. PATENT DOCUMENTS

| | | | |
|---|---|---|---|
| 4,238,840 A | | 12/1980 | Swainson |
| 4,365,357 A | * | 12/1982 | Draenert .................... 623/23.62 |
| 4,575,330 A | | 3/1986 | Hull |
| 4,595,006 A | * | 6/1986 | Burke et al. .................... 606/94 |
| 4,651,717 A | * | 3/1987 | Jakubczak .................... 128/899 |
| 4,972,006 A | | 11/1990 | Murphy et al. |
| 5,496,682 A | | 3/1996 | Quadir et al. |
| 5,519,816 A | | 5/1996 | Pomerantz et al. |
| 6,205,411 B1 | * | 3/2001 | DiGioia et al. ................. 703/11 |
| 6,488,638 B2 | | 12/2002 | Mushabac |

(Continued)

OTHER PUBLICATIONS

International Search Report for PCT/US06/43606 dated Jan. 17, 2008.

*Primary Examiner* — Elmer Chao
(74) *Attorney, Agent, or Firm* — Brooks Kushman P.C.

(57) ABSTRACT

A system and method for shaping an anatomical component having an existing shape and a desired reconstructed shape include an applicator for depositing material on the anatomical component and a controller in communication with the applicator, the controller controlling the deposition of material by the applicator based on a relationship between the applicator and the existing shape of the anatomical component to create the desired reconstructed shape.

40 Claims, 3 Drawing Sheets

(56) References Cited

U.S. PATENT DOCUMENTS

| | | |
|---|---|---|
| 6,520,964 B2 | 2/2003 | Tallarida et al. |
| 6,586,494 B2 | 7/2003 | Mejiritski et al. |
| 6,602,074 B1 | 8/2003 | Suh et al. |
| 6,641,772 B2 | 11/2003 | Gelbart |
| 6,711,432 B1 | 3/2004 | Krause et al. |
| 6,757,582 B2 * | 6/2004 | Brisson et al. ............... 700/186 |
| 6,827,723 B2 | 12/2004 | Carson |
| 7,618,451 B2 * | 11/2009 | Berez et al. ............... 623/14.12 |
| 2003/0040743 A1 * | 2/2003 | Cosman et al. ............... 606/41 |
| 2004/0068187 A1 | 4/2004 | Krause et al. |
| 2004/0176751 A1 | 9/2004 | Weitzner et al. |

\* cited by examiner

SYSTEM AND METHOD FOR SHAPING AN ANATOMICAL COMPONENT

CROSS-REFERENCE TO RELATED APPLICATIONS

This application claims the benefit of U.S. provisional application Ser. No. 60/734,857 filed Nov. 9, 2005.

BACKGROUND OF THE INVENTION

1. Field of the Invention

This invention relates to the field of computer-assisted surgery.

2. Background Art

In the knee joint, currently available techniques replace missing articular materials with grafts, implants, and other resurfacing techniques. These methods generally require approximate sizings, bone resections, and other general approximations of fit, size and function to achieve the desired result of a functional knee joint. More recent techniques require the pre-measurement of the defect area, manufacturing the replacement component to staff a library of components, and then trial fitting the component.

DETAILED DESCRIPTION OF THE INVENTION

As required, detailed embodiments of the present invention are disclosed herein; however, it is to be understood that the disclosed embodiments are merely exemplary of the invention that may be embodied in various and alternative forms. The figures are not necessarily to scale, and some features may be exaggerated or minimized to show details of particular components. Therefore, specific structural and functional details disclosed herein are not to be interpreted as limiting, but merely as a representative basis for teaching one skilled in the art to variously employ the present invention.

The system and method according to the present invention involve the building of three-dimensional structures in vivo to restore the degenerated areas associated with moderate to severe osteoarthritis as well as other deformities associated with advancing age, disease, or trauma found elsewhere in the body. Using the system and method of the present invention, the original shape and surface geometry and some portion of the original functionality of an anatomical component of the body may be restored in vivo at the time of surgery. The system and method may include selectively preparing the body surfaces, which may include the removal of existing materials and, subsequently or concurrently, depositing materials capable of bonding to themselves and to other substrates that may provide functional purpose to that area of the body.

In particular, image-guided computer aided surgery (CAS) information may be used to pre-map joint geometry to define an existing shape of the joint or a real-time measurement of the shape created, and then to guide an applicator that turns on and off based on its position in the joint. This system avoids the need for jigs or fixtures to aid in the preparation of the joint for surgical procedures. The image-guided CAS information may then be used to control the surface preparation, material application, and curing of a polymer, ceramic, biologic material or other material to a joint defect, thus enabling the surgeon to rebuild or resurface the joint with the applicator, such as by using an arthroscopic technique. The CAS information informs the applicator when to activate its various functions, such as to dispense and/or laser the polymer or other material, such that the surgeon may reconstruct the missing material onto the existing deformed surface by simply rubbing it across the defect and building it up until the CAS system stops dispensing the material. The applicator may be handheld or may be controlled with the assistance of a robotic arm or other similar programmable motion aid.

Figure 1:
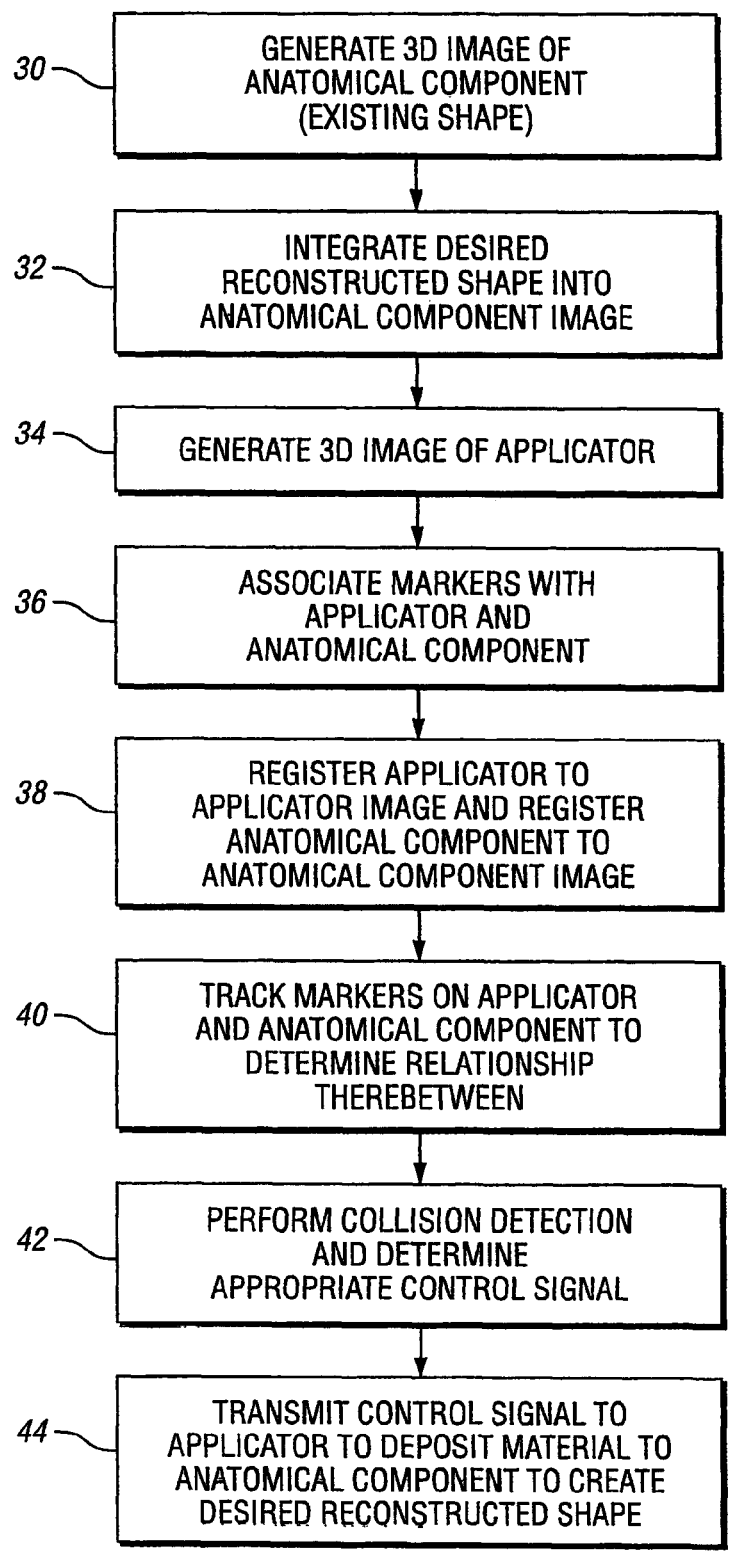
FIG. 1 is a flow chart of a method for shaping an anatomical component according to an aspect of the present invention.

With reference to FIG. 1, a method for shaping an anatomical component 10, such as bone, according to the present invention includes generating a 3D image 12 (existing shape) of anatomical component 10 at block 30, and integrating a desired reconstructed shape 14 of anatomical component 10 into the anatomical component image 12 at block 32. At block 34, the method includes providing an applicator 16 having a surface preparation/material deposition element 18, along with a 3D image 20 associated with applicator 16. At block 36, the method may further include associating markers 22, 23 with applicator 16 and anatomical component 10, and registering anatomical component 10 with the anatomical component image 12 and registering applicator 16 with the applicator image 20 as depicted at block 38. Still further, at block 40 the method according to the present invention may include tracking markers 22, 23 associated with anatomical component 10 and applicator 16 to determine a relationship therebetween, and at block 42 may include performing collision detection and determining an appropriate control signal for applicator 16. Based on the relationship, the method includes controlling applicator 16 by enabling applicator 16 to prepare a surface and then subsequently or concurrently add, deposit, or otherwise attach material to the existing shape 12 of anatomical component 10 and thus create the desired reconstructed shape 14 as shown at block 44.

Anatomical component 10 can include, but is not limited to, bone, cartilage, tendon, ligament, muscle, connective tissue, and fat. It is understood that the anatomical component 10, the existing shape 12, and the desired reconstructed shape 14 can be formed of living tissue or non-living materials. Furthermore, it is understood that the desired reconstructed shape 14 is not limited to a final restored shape of anatomical component 10, but may comprise any desired shape of anatomical component 10.

Figure 2:
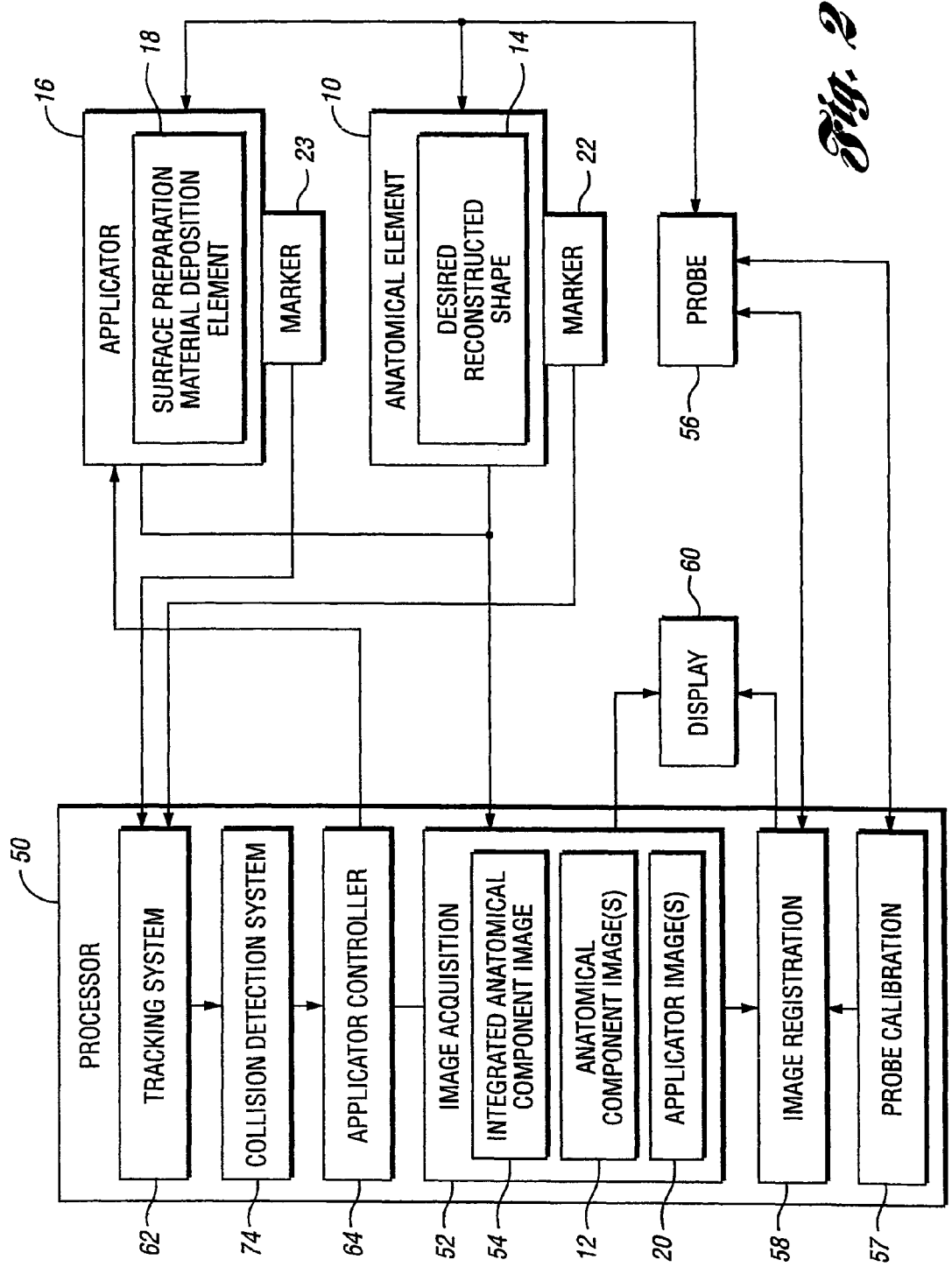
FIG. 2 is a block diagram of a system for shaping an anatomical component according to an aspect of the present invention.

With continued reference to FIGS. 1 and 2, anatomical component image 12, which may be a 3D image, can be provided or otherwise generated for input to a processor 50, such as within a computer. Image 12 may be acquired with a non-invasive means such as, but not limited to, a CT scan, CAD, MRI, ultrasound, fluoroscopy, x-ray, indirect measurement of the anatomic component via such methods as visual, sonic or RF range finding, or by direct contact measurement of the surface geometry, and the areas of deformity or disease can be mapped via computer-based modeling software. An image acquisition system 52 may be integrated with processor 50 as shown in FIG. 2, or alternatively can be distinct from processor 50 such that the image data can be transferred to processor 50. With the aid of software, the original contours of the missing articular and bony materials may be determined, such as in the case of a human knee. In addition, the anticipated kinematic and range of motion (ROM) information can be incorporated into the determination of the original joint shape. The desired reconstructed shape 14 can then be created to best fit the kinematic predictions as well as any other patient specific information that requires special attention. The 3D images of the desired reconstructed shape 14 may then be superimposed over the scanned 3D images of the existing shape 12 resulting in an integrated anatomical component image 54 that can be used to determine where material is to be applied within the joint.

Images 20 of applicator 16 can also be provided to processor 50. A probe 56 can be provided in communication with processor 50, wherein probe 56 can be calibrated via a probe calibration system 57 and employed to register the anatomical component image(s) 12 to anatomical component 10, and to register the applicator image(s) 20 to applicator 16. Image registration 58 can be performed by contacting discrete points on anatomical component 10 and applicator 16 with calibrated probe 56. Data provided by touching the surface of applicator 16 and anatomical component 10 can be compared with the image data from processor 50 which can associate the coordinates of applicator 16 and the anatomical component 10 to their respective image data.

Processor 50 can be provided in communication with a display 60 such that a 2D or 3D representation of the anatomical component image 12 and applicator image 20 can be presented on display 60, enabling a user to view relative positions of applicator 16 and anatomical component 10 and/or the existing shape 12 and the desired reconstructed shape 14.

The integrated anatomical component image 54 may be represented using volume pixels (voxels), and the voxels can be classified based on the existing shape 12 and the desired reconstructed shape 14. Likewise, the applicator image 20 may be represented using voxels, or instead may be provided as an image with certain dimensions, where such dimensions may be known relative to tracked positions on applicator 16 as further described below. Anatomical component 10 and applicator 16 could also be represented as surface models or other geometric models.

According to the present invention, a tracking system 62 in wireline or wireless communication with processor 50 can be used to track the relationship between applicator 16 and anatomical component 10 based on position data and/or angle data associated with applicator 16 and anatomical component 10. Tracking system 62 can include one or more first markers 22 associated with anatomical component 10, and one or more second markers 23 associated with applicator 16. Markers 22, 23 can be LEDs or other infrared sources, radio frequency (RF) sources, ultrasound sources, or other transmitters. Tracking system 62 can thus include a receiver (not shown), such as a camera system, to receive signals or other data from markers 22, 23 to track a position of anatomical component 10 based on the position of first marker(s) 22, and track a position of applicator 16 based on the position of second marker(s) 23, thus providing 3D tracking data to processor 50. Signal conditioners including filters, amplifiers, and analog-to-digital converters could also be utilized. Tracking system 62 can determine at least one position and at least one angle associated with anatomical component 10 and applicator 16, possibly tracking in three positions and three angles to provide six degrees of freedom. Inertial data, such as from accelerometers, may also be available to provide tracking data.

Processor 50 can include a representation of the existing shape 12 and the desired reconstructed shape 14 of anatomical component 10. By tracking anatomical component 10 and applicator 16, the system according to the present invention can transform the tracked positions of applicator 16 and anatomical component 10 to the applicator image(s) 20 and the anatomical component image(s) 12, respectively, to allow processor 50 to determine whether applicator 16 is in an appropriate location for performing its designated task, such as preparing the anatomical component for subsequent processing or depositing material to create the desired reconstructed shape 14. Furthermore, the classification of anatomical component voxels can be updated based on the tracking data, and tracking system 62 may include a predictive module to control applicator 16 or preparation/deposition element 18 by predicting the position, velocity, and/or acceleration of applicator 16 or preparation/deposition element 18 in a next measurement interval.

It is understood that the tracking system 62 described herein is merely one illustrative tracking system, and that other tracking systems can be used without departing from the scope of the present invention. In some embodiments, the voxel size and/or dimensions can match the tracking system accuracy, and those of ordinary skill in the art will recognize that tracking systems of any accuracies or resolutions can be utilized in accordance with the present invention.

Applicator 16 may be a handheld tool or be controlled with the assistance of a robotic arm or other programmable motion aid. Applicator 16 assists the surgeon in accurately depositing the material to create the desired reconstructed shape 14 of anatomical component 10, wherein applicator 16 is in either wireline or wireless communication with processor 50. Applicator 16 may be formed of plastic, metal, or another suitable material, and possibly include a lubricated coating to facilitate displacement of applicator 16. Prior to surgery, processor 50 is programmed with the desired reconstructed shape 14 for the bone or other anatomical component 10. During surgery, applicator 16 turns on and off automatically to allow the surgeon to perform the desired tasks such as surface preparation and the deposition of material to form the desired reconstructed shape 14. In particular, the function of applicator 16 may be completely controlled by processor 50 and an associated applicator controller 64, such that any active function of applicator 16, such as deposition of the materials as well as the curing of the materials, can only occur in the desired location and nowhere else. Processor 50 and applicator controller 64 are capable of controlling the on/off state of applicator 16 and the amounts and kinds of surface preparation and/or material deposition based on the location of applicator 16 relative to anatomical component 10 and the desired reconstructed shape 14. Knowing the positions of applicator 16 and anatomical component 10, processor 50 can calculate what part of anatomical component 10 that applicator 16 is touching and turn applicator 16 on and off at the proper times. Thus, with minimal visual necessity, the surgeon is able to perform the operation and the lost joint materials can be replaced with reasonable certainty of correctness.

Applicator 16 may include one or more surface preparation elements 18 that can adequately prepare the body surfaces in anticipation of material deposition and bonding. Such surface preparations may include, among many methods, chemical wash, laser ablation, mechanical abrasion, and others. Applicator 16 may include one or more deposition elements 18 that can add material to anatomical component 10. Applicator 16 is capable of carrying un-reacted monomers or polymers, or materials such as ceramics, metals, biological materials (e.g., mesenchymal stem cells), or others to the application site to be deposited onto the existing shape 12 to create the desired reconstructed shape 14. This may be accomplished by adding the material in small, discrete amounts capable of being cured, cross-linked, melted, sintered, sprayed on, plasma-deposited, or otherwise bonded or attached to the surface to be reconstructed as well as to itself. Applicator 16 is capable of incrementally building upon successive layers of materials, controlling each layer's properties such as thickness, shape and density to reach the final desired reconstructed shape 14. The desired reconstructed shape 14 can be a solid article, a porous article, a fibrous article, or a combination thereof.

Figure 3:
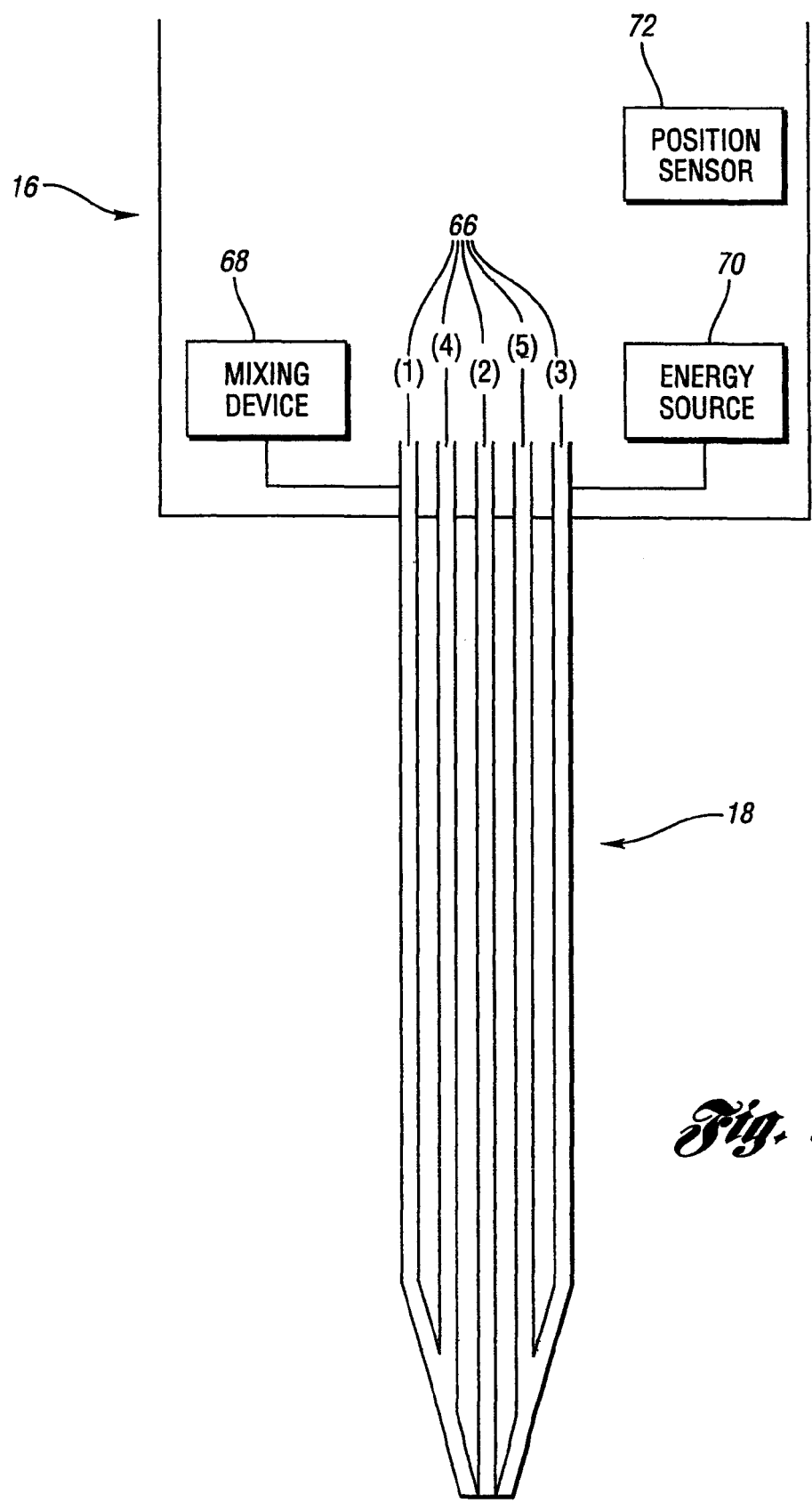
FIG. 3 is a cross-sectional view of an applicator according to an aspect of the present invention.

Applicator 16 can simultaneously deliver the resurfacing material(s) as well as bond them in place via various chemical, mechanical and adhesive means. Applicator 16 can also perform indirect measurement of the anatomical component 10 via such methods as visual, sonic, or RF range finding, or by direct contact measurement of the surface geometry. With reference to FIG. 3, according to one aspect of the present invention, applicator 16 may include a single or multiple channels 66, tubes, or the like (for example, but not limited to, the five channels depicted herein). According to one aspect of the present invention, applicator 16 may be a single-purpose applicator 16 for depositing material at the application site. According to another aspect of the present invention, applicator 16 may be a multi-purpose applicator 16, such as including a polymer dispenser in one channel 66 and a laser in another channel 66 to first prepare the surface and then subsequently cure the dispensed polymer via a cross-linking method. Applicator 16 may also include a mixing device 68 for mixing materials as either prior to or upon dispensation. Additionally, applicator 16 may include an activation energy or catalytic source 70 for adding energy to the material to initiate, accelerate, or otherwise promote the reaction of the material upon, or prior to, deposition at the application site. For example, applicator 16 could utilize lasers, hot air, conduction tubes, RF, IR, UV, ultrasound, catalysis, or others. One channel 66 may include a suction channel or port for applying suction to the application site (for example, but not limited to, site preparation) as an assistance to bonding, to remove debris, or as a means of applying pressure for consolidation or shaping of the desired reconstructed shape 14. Furthermore, applicator 16 can ablate, shave, scratch, drill or otherwise prepare the surface for materials bonding.

Applicator 16 can be a freehand instrument, although robotic control could also be utilized. For example, a robot could be utilized to add a predetermined shape to anatomical component 10, whereas manual control could be used to facilitate fine control of the material deposition to create the final desired reconstructed shape 14. Applicator 16 may include a position sensor 72 that is capable of collision detection via cooperation with a collision detection system 74 (FIG. 2), such that applicator 16 is capable of determining when the desired reconstructed shape 14 has been created or when additional materials need to be deposited. A computer-controlled cutting device could be used to remove unwanted anatomy such as osteophytes or to grind newly added material, or may be combined with applicator 16 as an additional, separate function. The use of multi-armed robotic control can allow for simultaneous surface preparation and deposition.

Pre-manufactured components such as, but not limited to, vascular stents, cardiac valves, artificial ligaments and tendons, K-wires, screws, plates, orthopedic joint replacement implants, or transplanted organ components can be incorporated into the guided surgical procedure as described herein. Thus, the system and method according to the present invention could be used to prepare anatomical component 10 for the subsequent implantation of a pre-manufactured component, or sub-assemblies of a larger finished component. In this way, the deposition of material may not necessarily complete the restoration of anatomical component 10, but rather may be a preliminary or intermediate part of the restoration process. Accordingly, a combination of computer-aided guidance, site preparation, and material augmentation (e.g., a bone graft in areas that are deficient) may be used in conjunction with the placement, mechanical attachment, in vivo assembly of, adhesive attachment of, or construction of the pre-manufactured component.

With reference to FIG. 2, applicator controller 64 transmits a control signal to applicator 16, where the control signal may include an analog signal or a digital signal. The control signal may be transmitted to a motor or other component of applicator 16. A preparation/deposition element 18 associated with applicator 16 can be controlled, such as to extend and retract the preparation/deposition element 18, to change the speed/deposition rate of the preparation/deposition element 18, to stop and start deposition of material by the preparation/deposition element 18, or another control.

Processor 50 can track anatomical component 10 and applicator 16, transform the tracking data to the image coordinates, and update the image(s)/voxels based on the new coordinates. Based on the computed positions of the first 22 and second markers 23 and the known respective geometries of applicator 16 and anatomical component 10, collision detection can be performed to compute a relationship between applicator 16 and at least part of anatomical component 10. Collision detection can allow processor 50 to compare the relative positions of applicator 16 and anatomical component 10 to determine whether applicator 16 is in an appropriate position for depositing material to create the desired reconstructed shape 14 of anatomical component 10. Based on the collision detection determination, a control signal can be provided to applicator 16, wherein the control signal can be based on the relative and/or predicted positions of anatomical component 10 to applicator 16, a measured and/or predicted velocity of applicator 16 and/or anatomical component 10, and other data. In one embodiment, the control signal may be at least partly based on a user-designated deposition precision, such that a user may designate relative precisions of deposition at different times.

For example, when applicator 16 is about to be located or is located in an area categorized as requiring material to create the desired reconstructed shape 14, a control signal may be transmitted to applicator 16 to cause the deposition element 18 to be activated or its speed varied. If it is determined that applicator 16 may be in a location which is not appropriate for depositing material to create the desired reconstructed shape 14, applicator controller 64 can transmit a control signal to applicator 16 which may cause applicator 16 to change its interaction with anatomical component 10, such as discontinuing operation of deposition element 18 or varying the speed of deposition element 18. In addition, deposition may also be modulated by slowing or stopping the delivery of material by at least partially closing a valve, stopping or slowing a pump, or diverting the material.

The properties of the deposited material can be selected to achieve a desired combination of strength, modulus, or other pertinent physical properties. The materials used in the system and method according to the present invention may able to support, if required, immediate weight bearing or other functional use. The materials utilized may be co-deposited with active materials such as pharmaceuticals, analgesics, lubricants, narcotics, live cell cultures, pre-cursors to enzymes, enzymes and proteins, and others, as well as pre-manufactured components.

Biodegradation of the deposited material at a predetermined rate may be acceptable in order to be replaced by cellular ingrowth, such as the use of anhydride chemistry described in U.S. Pat. No. 5,202,599. The desired reconstructed shape 14 can be assembled with deliberate voids which are suitable for cellular ingrowth (see, for example, U.S. Pat. No. 6,224,893). Live cells can be implanted at the time of fabrication of the desired reconstructed shape 14 (e.g., Zimmer Trabecular Metal™ technology). Friedmann et al. (*J Biomed Mater Res* 79A: 53-60, 2006) report the use of a ER:YAG laser that can be used to treat a surface in order to promote the attachment of osteoblasts. The deposition of elastomeric porous scaffolds such as one made from polyurethane has been demonstrated by Gorna and Gogolewski (*J Biomed Mater Res* 79A: 128-138, 2006).

The processes provided herein as residing on a computer or other processor-controlled device can be understood to be processes that can be implemented on one or more processors that can be one or more like or dissimilar devices. Components of the system can be viewed as modules that reside on or otherwise can be associated with one or more processors. The processor(s) can thus be embedded in one or more devices that can be operated independently or together in a networked environment, such as utilizing the Internet or another network. The devices that integrate with the processor(s) can include, for example, a personal computer, PDA, a cellular telephone, or another device capable of being integrated with a processor that can operate as provided herein. The present invention contemplates an arrangement wherein a CAS computer is connected to a remote operation site via a communication network, such as the Internet.

The method and system described herein are not limited to a particular hardware or software configuration, and can be implemented in hardware, software, or a combination thereof. The processor 50 can access one or more input devices to obtain input data, and can access one or more output devices to communicate output data. The input and/or output devices can include any storage device capable of being accessed by a processor 50 as provided herein such as, but not limited to, a hard drive, CD, DVD, memory stick, or others.

One of ordinary skill in the art will recognize that the method and system according to the present invention can utilize wired or wireless communications, or a combination thereof. Furthermore, those of ordinary skill in the art will recognize that the methods and systems disclosed herein have wide applicability to surgical and non-surgical techniques.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A system for building a three-dimensional structure in vivo to restore an anatomical component having an existing shape to a desired reconstructed shape, the system comprising:
   an applicator for depositing a material including at least one of a polymer, ceramic, metal, or biological material on the existing shape of the anatomical component; and
   a controller in communication with the applicator, the controller controlling the applicator to add successive layers of the material of controlled thickness onto the existing shape of the anatomical component to create the desired reconstructed shape of the anatomical component and restore at least a portion of an original function of the anatomical component.

2. The system according to claim 1, further comprising a tracking system in communication with the applicator, the controller, and the anatomical component for obtaining tracking data indicating a relationship between the applicator and the anatomical component.

3. The system according to claim 2, wherein the tracking system is configured to obtain tracking data using at least one first marker associated with the anatomical component and at least one second marker associated with the applicator.

4. The system according to claim 2, wherein the relationship between the applicator and the anatomical component is based on at least one of position data and angle data.

5. The system according to claim 4, wherein the tracking system is configured to obtain tracking data based on at least three positions and at least three angles.

6. The system according to claim 1, further comprising an image acquisition system in communication with the controller that utilizes at least one image associated with the anatomical component and at least one image associated with the applicator to control material deposition by the applicator, the at least one anatomical component image including an image associated with the existing shape and an image associated with the desired reconstructed shape.

7. The system according to claim 6, wherein the at least one anatomical component image is registered to the anatomical component, and the at least one applicator image is registered to the applicator.

8. The system according to claim 6, further comprising a display in communication with the image acquisition system for displaying the at least one anatomical component image and the at least one applicator image.

9. The system according to claim 1, wherein the applicator is handheld.

10. The system according to claim 1, wherein the applicator is under robotic control.

11. The system according to claim 1, wherein the applicator includes a material deposition element for depositing material on the anatomical component.

12. The system according to claim 1, wherein the applicator includes a surface preparation element for preparing the anatomical component for material deposition.

13. The system according to claim 1, wherein the applicator includes at least one energy source.

14. The system according to claim 1, wherein the applicator is arranged to bond or cure the deposited material.

15. The system according to claim 1, wherein the applicator includes a mixing device for mixing the materials to be deposited.

16. The system according to claim 1, wherein the applicator includes a lubricated coating to facilitate displacement.

17. The system according to claim 1, wherein the applicator includes one or more channels arranged to receive material to be deposited.

18. The system according to claim 1, wherein the applicator includes a suction port.

19. A method for building a three-dimensional structure in vivo to restore an anatomical component having an existing shape to a desired reconstructed shape, the method comprising:
   providing an applicator for depositing a material including at least one of a polymer, ceramic, metal, or biological material on the existing shape of the anatomical component;
   controlling the applicator to add successive layers of the material of controlled thickness onto the existing shape of the anatomical component to create the desired reconstructed shape of the anatomical component and restore at least a portion of an original function of the anatomical component.

20. The method according to claim 19, further comprising obtaining tracking data indicating a relationship between the applicator and the anatomical component.

21. The method according to claim 20, wherein obtaining tracking data includes using at least one first marker associated with the anatomical component and at least one second marker associated with the applicator.

22. The method according to claim 20, wherein obtaining tracking data includes determining at least one position and at least one angle associated with at least one of the anatomical component and the applicator.

23. The method according to claim 22, wherein obtaining tracking data includes obtaining data based on at least three positions and at least three angles.

24. The method according to claim 19, further comprising utilizing at least one image associated with the anatomical component and at least one image associated with the applicator to control material deposition by the applicator, the at least one anatomical component image including an image associated with the existing shape and an image associated with the desired reconstructed shape.

25. The method according to claim 24, further comprising displaying the at least one anatomical component image and the at least one applicator image.

26. The method according to claim 24, further comprising registering the at least one anatomical component image to the anatomical component, and registering the at least one applicator image to the applicator.

27. The method according to claim 24, further comprising superimposing the image of the desired reconstructed shape over the image of the existing shape, resulting in an integrated anatomical component image that can be used to determine where material is to be deposited on the anatomical component.

28. The method according to claim 19, further comprising using kinematic and range of motion information to create the desired reconstructed shape.

29. The method according to claim 19, wherein controlling the applicator includes extending and retracting a surface preparation/material deposition element associated with the applicator.

30. The method according to claim 19, wherein controlling the applicator includes changing the speed or deposition rate of a surface preparation/material deposition element associated with the applicator.

31. The method according to claim 19, wherein controlling the applicator includes turning the applicator on and off to control the deposition of material based on the position of the applicator relative to the anatomical component.

32. The method according to claim 19, further comprising co-depositing active materials with materials for creating the desired reconstructed shape.

33. The method according to claim 19, wherein controlling the applicator includes incrementally building upon successive layers of materials to create the desired reconstructed shape.

34. The method according to claim 19, further comprising preparing the anatomical component for material deposition.

35. The method according to claim 19, further comprising bonding or curing the deposited material using the applicator.

36. The method according to claim 19, further comprising mixing the materials to be deposited using the applicator.

37. The method according to claim 19, further comprising implanting a pre-manufactured component or organ replacement.

38. The method according to claim 19, further comprising using the applicator to prepare and assemble pre-manufactured sub-assemblies into a larger finished component.

39. The method according to claim 19, further comprising using the applicator to prepare and transplant complete or partial organ replacements.

40. A system for building a three-dimensional structure in vivo to restore an anatomical component having an existing shape to a desired reconstructed shape, the system comprising:
   an applicator for depositing a material including at least one of a polymer, ceramic, metal, or biological material on the existing shape of the anatomical component; and
   a controller in communication with the applicator, the controller controlling the applicator to add successive layers of the material of controlled thickness onto the existing shape of the anatomical component to create the desired reconstructed shape of the anatomical component, the desired reconstructed shape being one of solid, porous or fibrous article.

* * * * *